United States Patent [19]

Barnea

[11] Patent Number: 5,233,990
[45] Date of Patent: Aug. 10, 1993

[54] METHOD AND APPARATUS FOR DIAGNOSTIC IMAGING IN RADIATION THERAPY

[76] Inventor: Gideon Barnea, 7887 E. Uhl St., No. 410, Tucson, Ariz. 85710

[21] Appl. No.: 819,957

[22] Filed: Jan. 13, 1992

[51] Int. Cl.⁵ .............................................. A61B 5/05
[52] U.S. Cl. .................................. 128/653.1; 378/65
[58] Field of Search ........................ 128/653.1; 378/65

[56] References Cited

U.S. PATENT DOCUMENTS

| | | | |
|---|---|---|---|
| 3,783,251 | 1/1974 | Pavkovich | 378/65 |
| 4,123,660 | 10/1978 | Horwitz | 378/65 |
| 4,930,509 | 6/1990 | Brisson | 128/653.1 |

OTHER PUBLICATIONS

Droege, R. T. et al., "Influence of Metal Screens on Contrast in Megavoltage X-Ray Imaging," Med. Phys. 6, 487-492, 1979.
Lutz, W. R. et al., "A Test Object for Evaluation of Portal Film" Int. J. Radiat. Oncol. Biol. Phys. 11, 631-634, 1985.
Munro, P. et al., "Therapy Imaging: A Signal-to-Noise Analysis of Metal Plate/Film Detectors," Med. Phys. 14, 975-984, 1987.
Mark, J. E. et al., "The Value of Frequent Treatment Verification Films in Reducing Localization Error in the Irradiation of Complex Fields," Cancer, 37, 2755-2761, 1976.
Huizenga et al. "Accuracy in Radiation Field Alignment in Head and Neck Cancer: A Prospective Study," Rad. Oncol. 11, 181-187, 1988.
Pearcy et al., "The Impact of Treatment Errors on Post-Operative Radiotherapy for Testicular Tumors," Br. J. Radiol. 58, 1003-1005, 1985.
Rabinowitz et al. "Accuracy of Radiation Field Alignment in Clinical Practice," Int. J. Radiat. Oncol. Biol. Phys. 11, 1857-1867, 1985.
Lam et al. "On-Line Measurement of Field Placement Errors in External Beam Radiotherapy," Br. J. Radiol. 60, 361-367, 1987.
Baily et al. "Fluoroscopic Visualization of Megavoltage Therapeutic X-Ray Beams," Int. J. Radiat. Oncol. Biol. Phys. 6, 935-939, 1980.
Herk et al., "A Digital Imaging System for Portal Verification," in The Use of Computers in Radiation Therapy, I. Brunvis Ed., North Holland, 371-373, 1987.

(List continued on next page.)

Primary Examiner—Lee S. Cohen
Assistant Examiner—Samuel Gilbert
Attorney, Agent, or Firm—Antonio R. Durando; Harry M. Weiss

[57] ABSTRACT

An apparatus for diagnostic and verification imaging in radiation therapy that consists of attachments for standard radiotherapy equipment comprising an x-ray tube and an x-ray detector placed on opposite sides of a patient along the main axis of the beam produced by the treatment unit. The detector is placed on a plane orthogonal to the axis of the treatment beam and between the beam source and the patient, while the x-ray tube is placed on the other side of the patient, coaxially with the treatment beam and facing the detector. As a result of this configuration, the radiographic view of the x-ray beam, as seen on the detector, is equivalent to the view produced on the same detector by the therapeutic beam, varied only by parallax deviations that can be corrected by geometrical calculations. Accordingly, x-ray exposures and real-time verification of the position of a patient can be obtained with the same unit used for treatment and without requiring movement of either patient or equipment. In addition, the apparatus enables a user to produce diagnostic images that can be used directly to manufacture shielding blocks in conventional shielding-block cutters.

10 Claims, 2 Drawing Sheets

OTHER PUBLICATIONS

Shalev et al. "Video Techniques for On-Line Portal Imaging," Comp. Med. Imag. Graph. 13, 217-226, 1989.

Munro et al. "A Digital Fluoroscopic Imaging Device for Radiotherapy Localization," Int. J. Radiat. Oncol. Biol. Phys. 18, 641-649, 1990.

Durham et al. "Portal Film Quality: A Multiple Institutional Study," Med. Phys. 11, 555-557, 1984.

Biggs et al. "A Diagnostic X-Ray Field Verification Device for a 10 MV Accelerator," Int. J. Radiat. Oncol. Biol. Phys. 11, 635-643, 1985.

Marks J. E. et al. "Localization in the Radiotherapy of Hodgkins Disease and Malignant Lymphoma with Extended Mantle Fields," Cancer 34, 83-90, 1974.

Marks J. E. et al. "Dose-Response Analysis for Nasopharyngeal Carcinoma: An Historical Perspective," Cancer 50, 1042-1050 1982.

White J. E. et al. "The Influence of Radiation Therapy Quality Control on Survival, Response and Sites of Relapse in Oat Cell Carcinoma of the Lung, " Cancer 50, 1084-1090, 1982.

Kinzie J. J. et al. "Patterns of Care Study: Hodgkins Disease Relapse Rates and Adequacy of Portals, " Cancer 52, 2223-2226, 1983.

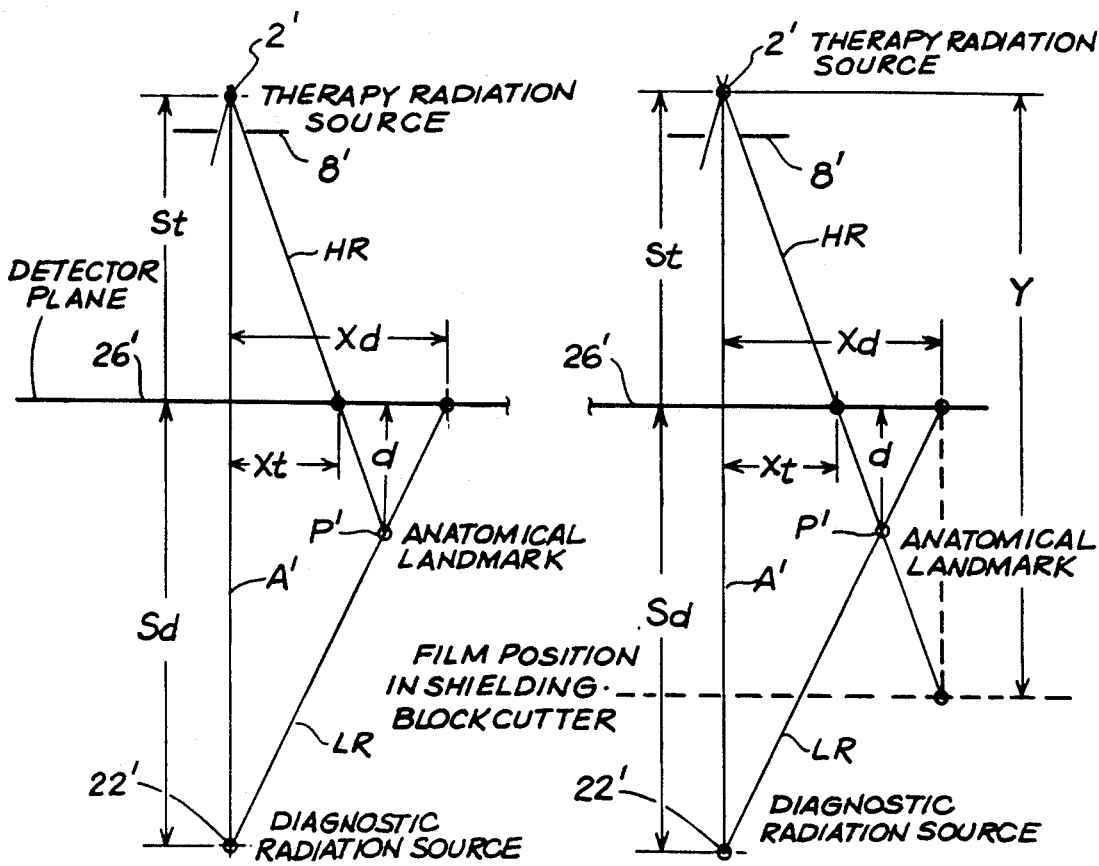
Fig. 3  Fig. 4
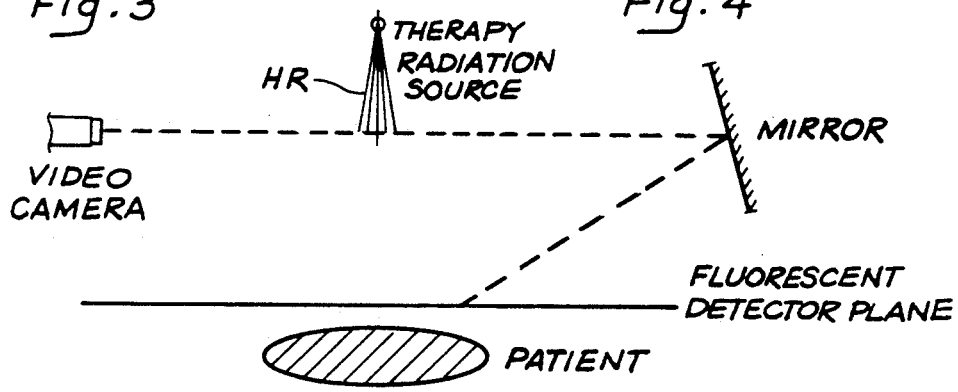
Fig. 5

METHOD AND APPARATUS FOR DIAGNOSTIC IMAGING IN RADIATION THERAPY

BACKGROUND OF THE INVENTION

1. Field of the Invention

This invention is related to the general field of radiation imaging for medical applications. In particular, the invention provides a new method and apparatus for producing a diagnostic image of the portion of the body affected by a tumor, so that the required dosage of radiation can be accurately delivered to the prescribed target volume.

2. Description of the Prior Art

The main object of radiotherapy is to deliver the prescribed dosage of radiation to a tumor in a patient while minimizing the damage to surrounding, healthy, tissue. Since very high energy radiation (produced at 4 to 25 million volts, typically generated by a linear accelerator) is normally used to destroy tumors in radiotherapy, the high energy is also destructive to the normal tissue surrounding the tumor. Therefore, it is essential that the delivery of radiation be limited precisely to the prescribed target volume (i.e., the tumor plus adequate margins), which is accomplished by placing appropriately constructed shielding blocks in the path of the radiation beam. Thus, the goal is to accurately identify the malignancy within the body of the patient and to target the prescribed dosage of radiation to the desired region on the immobilized patient.

To that end, the ideal procedure requires the identification of the exact anatomical location of the tumor and the corresponding accurate positioning of the radiation field during treatment. This could be easily achieved if it were possible to locate and treat the tumor at the same time. In practice, though, this is not possible because the equipment used to identify the tumor (x-ray machine, computed tomography equipment, or the like) is separate from the equipment used for the therapeutical irradiation of the patient, requiring the movement and repositioning of the patient from one piece of equipment to the other. As illustrated in schematic form in FIG. 1, a conventional treatment unit 10 consists of a linear accelerator (linac) head 2 mounted on a gantry 4 so that its collimated high-energy emissions HR irradiate a patient P lying on a gurney 6 directly below through shielding blocks 8 attached to the head. A bracket 12 supporting a detector 14 may be mounted on the opposite side of the head within the field of radiation in order to take radiographs of the patient being treated. The gantry 4 is movable around a pivot 16 to permit the rotation of the head (and of the detector) around the patient to afford different views of the area to be treated ("multiple fields" treatment). The normal procedure involves the use of a diagnostic simulator, which is a diagnostic x-ray machine with the same physical characteristics of the radiation therapy machine (schematically also represented by FIG. 1, where a diagnostic x-ray head replaces the linac head 2), so that the field of view of the low-energy x rays emitted in the simulator is the same as that of the high-energy radiation emitted in the radiation therapy machine. Prior to treatment, the patient is radiographed using the simulator and an image of the target area is obtained with low-energy radiation (in the order of 100 kVp), which yields good image quality. The exact target volume is then delineated on the radiograph by a physician and matching shielding blocks are constructed to limit the field of view of the irradiating machine to the region so delineated. A mold of the shielding blocks is first cut out of plastic material (normally polystyrene) with a shielding-block cutter, a machine that reproduces exactly the relative positions of the linac head, the shielding blocks and the detector as they stand in the treatment unit. By using mechanical means, the shielding blocks are cut so that the field of irradiation from the treatment unit will corresponds exactly to the area delineated by the physician on the diagnostic radiograph. The final shielding blocks are then made from the mold with lead alloys that attenuate considerably the propagation of radiation. Thus, the shielding blocks function as templets that limit the radiation treatment to the areas left open within the contour of the shielding blocks. In addition, it is common practice to mark the skin of a patient with reference markings that are used in aligning the position of the patient with the field of emission of the radiation therapy machine.

These apparently sound procedures in fact suffer from serious practical shortcomings. Errors in positioning the shielding blocks between the radiating source and the patient, as well as incorrect beam alignment and patient movement, all have a cumulative effect reducing the accuracy of the procedure. Even the markings on the skin of the patient may be the cause of alignment problems because of shifting of the skin with respect to the patient's internal anatomy as a result of body motion or, over a period of time, even of body changes. Thus, the area actually irradiated during the therapeutic session often does not correspond to the area delineated in the radiograph generated by the simulator.

Positioning errors during irradiation have been found to have very serious consequences for the successful prognosis of the treatment. For example, researchers have been able to correlate the recurrence of lymphoma to such positioning errors (J. E. Marks, A. G. Haus, H. G. Sutton and M. L. Griem, "Localization Error in the Radiotherapy of Hodgkin's Disease and Malignant Lymphoma with Extended Mantle Fields," Cancer 34, 83-90, 1974); and it has been found that improved tumor control of nasopharingeal carcinomas can be related to greater accuracy in the delivery of calculated dosages of radiation (J. E. Marks, J. M. Bedwinek, F. Lee, J. A. Purdy and C. A. Perez, "Dose-Response Analysis for Nasopharyngeal Carcinoma: An Historical Perspective," Cancer 50, 1042-1050, 1982). Similarly, it has been found that shielding inaccuracies have resulted in significantly lower primary tumor control and survival of patients of oat cell lung cancer (J. E. White, T. Chen, J. McCracken, P. Kennedy, H. G. Seydel, G. Hartman, J. Mira, M. Khan, F. Y. Durrance and 0. Skinner, "The Influence of Radiation Therapy Quality Control on Survival, Response and Sites of Relapse in Oat Cell Carcinoma of the Lung," Cancer 50, 1084-1090, 1982); and that the local recurrence of Hodgkin's disease was significantly higher when the radiation field did not adequately cover the tumor (J. J. Kinzie, G. E. Hanks, C. J. Maclean and S. Kramer, "Patterns of Care Study: Hodgkin's Disease Relapse Rates and Adequacy of Portals," Cancer 52, 2223-2226, 1983).

The only technique widely used today to check the accuracy of the radiation field is by imaging with the radiotherapy beam itself at the time of treatment. Prior to treatment, a "portal" image is obtained by using the therapy beam (at high energy) and the resulting exposure is visually compared with that taken with the simulator (at low energy). This technique is therefore known as "portal imaging" or "therapy verification," and is repeated periodically during the period of radiation treatment. Unfortunately, though, because of the high-energy radiation emitted by the treatment beam (produced at 4-25 million volts), the resulting portal images have poor resolution and show very poor contrast between soft tissues and bones, often making the images totally unsuited for verification by comparison with the low-energy images produced by the simulator. See, for example, R. T. Droege and B. J. Bjarngard, "Influence of Metal Screens on Contrast in Megavoltage X-Ray Imaging," Med. Phys. 6, 487-492, 1979; L. E. Reinstein, M. Durham, M. Tefft, A. Yu and A. S. Glicksman, "Portal Film Quality: A Multiple Institutional Study," Med Phys. 11, 555-557, 1984; W. R. Lutz and B. E. Bjarngard, "A Test Object for Evaluation of Portal Film," Int. J. Radiat. Oncol. Biol. Phys. 11, 631-634, 1985; and P. Munro, J. A. Rawlinson and A. Fenster, "Therapy Imaging: A Signal-to-Noise Analysis of Metal Plate/Film Detectors," Med. Phys. 14, 975-984, 1987. Indeed, positioning errors occur very frequently in spite of the use of portal images. See J. E. Marks, A. G. Haus, H. G. Sutton and M. L. Griem, "The Value of Frequent Treatment Verification Films in Reducing Localization Error in the Irradiation of Complex Fields," Cancer 37, 2755-2761, 1976; R. W. Byhardt, J. D. Cox, A. Hornburgh and G. Liermann, "Weekly Localization Films and Detection of Field Placement Errors," Int. J. Radiat. Oncol. Biol. Phys. 4, 881-887, 1978; Huizenga, P. C. Lenendag, P. M. Z. R. De Porre and A. G. Visser, "Accuracy in Radiation Field Alignment in Head and Neck Cancer: A Prospective Study," Rad. Oncol. 11, 181-187, 1988; R. G. Pearcy and S. E. Griffiths, "The Impact of Treatment Errors on Post-Operative Radiotherapy for Testicular Tumors," Br. J. Radiol. 58, 1003-1005, 1985; I. Rabinowitz, J. Broomberg, M. Goitein, K. McCarthy and J. Leong, "Accuracy of Radiation Field Alignment in Clinical Practice," Int. J. Radiat. Oncol. Biol. Phys. 11, 1857-1867, 1985; and W. C. Lam, M. Partowmah, D. J. Lee, M. D. Wharam and K. S. Lam, "On-Line Measurement of Field Placement Errors in External Beam Radiotherapy," Br. J. Radiol. 60, 361-367, 1987. Imaging devices other than X-ray film have been used in an attempt to improve the quality of the image produced during therapy verification. These include metal and fluorescent screens in contact with conventional film, and non-film imaging processes and devices such as xeroradiography, liquid ionization chambers, fluoroscopic imaging, linear diode arrays, photostimulable phosphors, and others. In addition, various image processing techniques (both analog and digital) have been used to enhance the quality of the final verification image; but all these methods and devices have resulted only in a limited success in yielding a good quality, and therefore useful, diagnostic image. Real-time portal imaging using video techniques has also been proposed, so that patient movement can be monitored during treatment. Because they all use the high-energy therapy beam as the source of radiation, though, the quality of the image remains poor. See N. A. Baily, R. A. Horn and T. D. Kampp, "Fluoroscopic Visualization of Megavoltage Therapeutic X-Ray Beams," Int. J. Radiat. Oncol. Biol. Phys.6, 935-939, 1980; M. V. Herk and H. Meertens, "A Digital Imaging System for Portal Verification," in "The Use of Computers in Radiation Therapy," I. Brunvis Ed., North Holland, 371-373, 1987; S. Shalev, T. Lee, K. Leszczynski, S. Cosby and T. Chu, "Video Techniques for On-Line Portal Imaging," Comp. Med. Imag. Graph. 13, 217-226, 1989; and P. Munro, J. A. Rawlinson and A. Fenster, "A Digital Fluoroscopic Imaging Device for Radiotherapy Localization," Int. J. Radiat. Oncol. Biol. Phys. 18, 641-649, 1990. A survey of 23 different radiotherapy departments shows that at each of eight institutions (i.e., 35 percent of the 23 institutions sampled) more than ⅜ of the submitted portals were evaluated as poor in quality. Furthermore, it shows that approximately one-half of the institutions were producing poor-quality films at a rate of at least 50 percent. See Reinstein, L. E., M. Durham, M. Tefft, A. Yu, and A. S. Glicksman, "Portal Film Quality: A Multiple Institutional Study," Med. Phys. 11, 555-557, 1984.

Another, logical, approach to obtaining diagnostic quality portal films has been by mounting an x-ray tube on the head of the treatment unit as close to the linac gantry as possible. See P. J. Biggs, M. Goitein and M. D. Russell, "A Diagnostic X-Ray Field Verification Device for a 10 MV Accelerator," Int. J. Radiat. Oncol Biol. Phys. 11, 635-643, 1985. The x-ray tube is aligned with the linac emission field so that, to the extent possible within the physical constraints of both devices, the x-ray emissions have the same field of view of the high-energy radiation. As a result, the image received on a film placed on a detector tray on the opposite side of the patient by exposure to either source of radiation is theoretically almost exactly the same. In order to implement this approach, though, a special shielding-block holder coupled to the gantry has to be made, disabling the normal rotation of the linac's collimator and limiting the adjustment capabilities of the equipment. Thus, the complexity of the procedure, the oblique view of the diagnostic beam and the increased time required for each treatment have prevented this technique from gaining widespread acceptance. Furthermore, this method is unsuited for real-time portal imaging.

A similar approach has been followed by placing an x-ray tube at a fixed angle with respect to the axis of the therapeutic beam, so that the x-ray beam and the therapeutic beam have coinciding isocenters corresponding to the location of the radiation target. By rotating the gantry of the radiation unit by that angle, the target can be irradiated from the same point either with a treatment beam or an x-ray beam, with every other variable remaining unchanged. Therefore, verification can be obtained simply by rotating the gantry and switching from one mode of operation to the other. The main problem with this approach is the inevitable angular error introduced during the rotation of the gantry. In addition, because of the alternative use of either mode of operation, this equipment is also not suitable for real time verification.

Therefore, it would be very desirable to have a simpler and more accurate verification imaging system for radiation therapy verification, especially for real time applications. This invention relates to the use of a conventional x-ray tube and conventional imaging devices in a novel geometric configuration to produce such an improved verification imaging system.

BRIEF SUMMARY OF THE INVENTION

One objective of this invention is the development of therapy verification apparatus that produces verification images of the same quality obtained with diagnostic apparatus.

Another objective of the invention is an imaging apparatus that can be implemented as an accessory to existing radiation-therapy treatment units.

A further goal of the invention is an imaging apparatus and technique that are suitable for on-line, real time, applications in conjunction with radiation treatments.

Still another objective of the invention is an apparatus that, as a result of the position of the x-ray emission source, produces an image corresponding to the same field of view of the linac beam used in conjunction with it.

A final objective of this invention is the realization of the above mentioned goals in an economical and commercially viable manner. This is done by utilizing components and methods of manufacture that are either already available in the open market or can be developed at competitive prices.

According to these and other objectives, the present invention consists of attachments for standard radiotherapy equipment comprising an x-ray tube and an x-ray detector placed on opposite sides of a patient along the main axis of the beam produced by the treatment unit. The detector is placed on a plane orthogonal to the axis of the treatment beam and between the beam source and the patient, while the x-ray tube is placed on the other side of the patient, coaxially with the treatment beam and facing the detector. As a result of this configuration, the radiographic view of the x-ray beam, as seen on the detector, is equivalent to the view produced on the same detector by the therapeutic beam, varied only by parallax deviations that can be corrected by geometrical calculations. Accordingly, x-ray exposures and real-time verification of the position of a patient can be obtained with the same unit used for treatment and without requiring movement of either patient or equipment.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

BRIEF DESCRIPTION OF THE DRAWINGS

FIG. 3 is a diagrammatic representation of the geometrical relationship of the various points of interest in the apparatus of FIG. 2.

FIG. 4 shows, with reference to the geometry of the therapeutic unit represented in FIG. 3, the distance at which a diagnostic image must be positioned from the simulated radiation source's position in a shielding-block cutter in order to have perfect correspondence with a picture produced with a simulator.

FIG. 5 illustrates in schematic form the us of a fluorescent screen detector in conjunction with a mirror and a video camera to produce real-time verification images with the apparatus of the invention.

DETAILED DESCRIPTION OF THE INVENTION

The heart of this invention lies in the recognition that verification of the correct position of a patient during treatment can be achieved by placing a detector between the treatment beam source and the patient, and placing an x-ray tube along the axis of the treatment beam on the opposite side of the patient. Given the position of the various components, a fixed geometrical relationship exists that permits the direct construction of verification images for immediate use during treatment.

Figure 1:
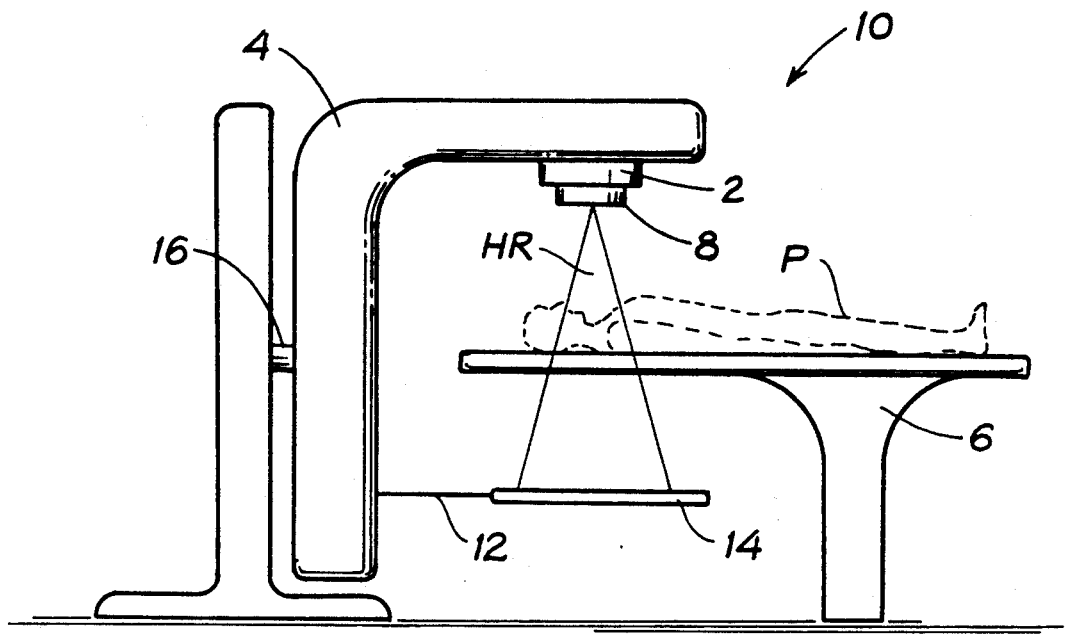
FIG. 1 is an elevational schematic representation of a typical radiation therapy unit.
Figure 2:
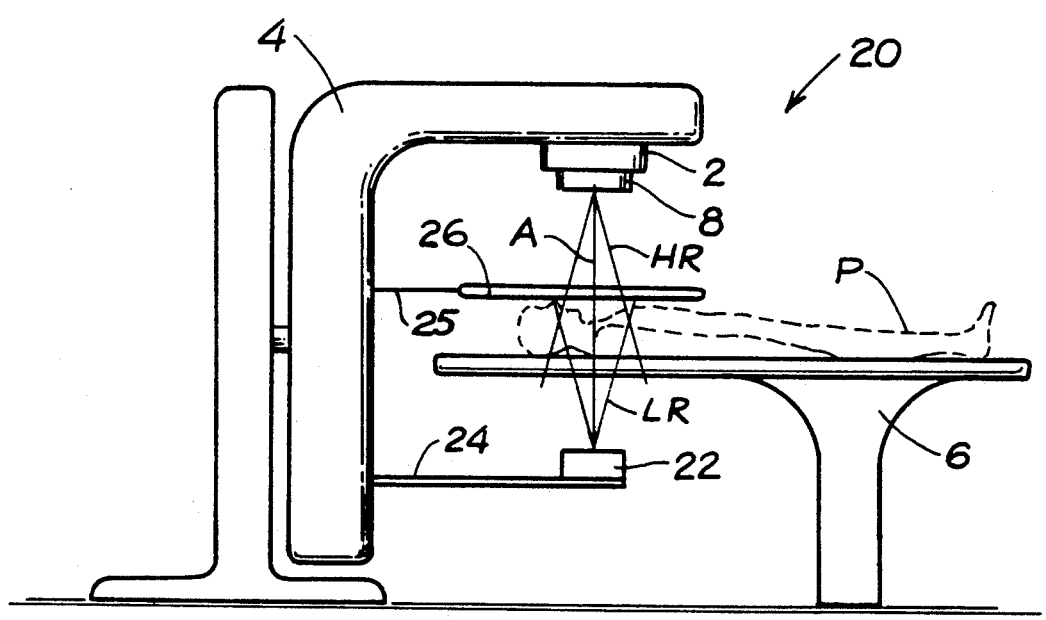
FIG. 2 is an elevational schematic representation of the apparatus of the present invention, illustrated as an attachment to the typical radiation therapy unit shown in FIG. 1.

Referring to the drawings, wherein like parts are identified with like symbols and numerals throughout this specification, FIG. 2 illustrates in schematic elevational representation the verification apparatus 20 of this invention, shown as an attachment to a standard radiation treatment unit (as illustrated in FIG. 1). An x-ray tube 22 is mounted on a support bracket 24 on the bottom side of the gantry 4, possibly replacing the detector 14 shown in FIG. 1. The x-ray tube is positioned facing up along the axis A of the beam radiated by the linac head 2, so that the axis of the x-ray beam is coaxial with that of the treatment beam. At the same time, a bracket 25 supporting a detector 26 is mounted on the gantry (or otherwise placed in the same position) between the patient P and the linac head, as close to the patient as practicable. Thus, the detector 26 may be exposed either to the high-energy beam HR produced by the linear accelerator head 2 or to the low-energy beam LR (x rays) produced by the x-ray tube 22, or to both beams at the same time.

FIG. 3 is a diagrammatic representation of the geometrical relationship of the various points of interest in the apparatus of FIG. 2. Point 2' represents the location of the source of high-energy radiation HR emitted by the linac head 2 and contained by the boundary 8' of the shielding blocks 8; similarly, point 22' corresponds to the location of the coaxial source of low-energy radiation LR emitted by the x-ray tube 22; and the line A' corresponds to the axis common to the two beams. Line 26' represents the location of the detector 26 and point P' represents a point at the boundary of the target volume. $S_t$ and $S_d$ are the distances of the high-energy radiation source (therapeutic) and the low-energy radiation source (diagnostic), respectively, from the detector. Obviously, the view of point P' on the detector 26', as projected by the x-ray beam, is different from the view seen on the same plane by the treatment beam. Point P' is projected a distance $X_d$ from the axis by the diagnostic beam (LR), but it is seen (back-projected) at a distance $X_t$ from the axis by the treatment beam (HR). The relationship between $X_d$ and $X_t$ is a function of the distance d between the detector 26' and the point P', the two being obviously the same for d=0. Simple trigonometry permits the determination of the following general relationship between these variables:

$$X_d = X_t(1+d/S_t)/(1-d/S_d), \tag{1}$$

where $S_t$ and $S_d$ are the distances of the high-energy radiation source and the low-energy radiation source, respectively, from the detector.

Therefore, for a given physical configuration of the equipment (i.e., for given values of $S_d$, $S_t$ and d), the relationship between any point in the image created by the x-ray tube and the location of the same point in the corresponding image seen on the detector by the therapeutic beam is linear and fixed. That is, one can be obtained from the other by a simple parallax correction according to the equation given above. Therefore, the field of view of the therapeutic beam on the detector can be correlated to the image projected on the plane by the diagnostic beam by a simple computation, and the two fields of view can be compared for verification purposes.

In practice, shielding blocks will have been manufactured as outlined above and the verification task before treatment is directed at ensuring that the treatment beam, as attenuated by the blocks, is irradiating the target area delineated in the original diagnostic picture. If that picture was taken using a conventional simulator (i.e., an x-ray machine with the exact same geometry of the treatment unit), the shielding blocks are developed by conventional techniques so that the outline of the permitted field of view of the treatment beam coincides with the area delineated by the physician on the diagnostic image. If, for example, point P' corresponds to a point in the diagnostic image outlined by the physician as a boundary for radiation, the shielding blocks are shaped to permit the treatment beam to irradiate the area between the axis A' and point P' only, and the object of verification is to see whether that point is indeed at the boundary of the therapeutic beam during treatment. As mentioned above, current practice involves taking a picture with the high-energy treatment beam and a detector below the patient, so that the new image can in theory be compared with the diagnostic image. Unfortunately, though, the poor quality of the image obtained with the high-energy treatment beam renders it, in many cases, nearly useless in practice.

The present invention addresses this problem by producing a coaxial image taken with an x-ray machine. By creating an x-ray image on the detector 26 through exposure to a low-energy beam from the tube 22, a good quality image of a patient's anatomy is obtained that can be corrected by the parallax relationship given above to produce an exact replica of the corresponding image seen by the therapeutic beam. Therefore, the resulting corrected picture is in the same scale of, and can be directly compared with, the original diagnostic image outlined for targeting the treatment area. As this can be done just before treatment, when the patient is positioned for therapeutic irradiation, it can be an extremely useful tool for therapy verification. In addition, the verification image can be superimposed on an image obtained by exposing the detector on the plane 26' to the shielded therapeutic beam, which in practice will only show the contour of the shield (i.e., the boundary of the radiation field) because of the high-energy radiation. These two pictures combined correspond exactly to the field of radiation currently targeted by the treatment beam. Therefore, they provide the radiotherapist with a current verification of the area targeted for treatment.

According to another method of use of the apparatus of this invention, it is possible to use the x-ray tube 22 also for the initial diagnostic image (normally taken on film); that is, it may be used as a substitute for the conventional simulator. In that case, the position of the diagnostic film in the shielding-block cutter can be adjusted to permit its use to cut the shielding blocks as if the diagnostic image had been produced by a simulator. As would be obvious to one skilled in the art, FIG. 4 shows that for a given geometry of the therapeutic unit, taken for example as illustrated in FIG. 3, there exists a distance Y at which the film must be positioned from the simulated high-energy radiation source's position in the shielding-block cutter in order to have perfect correspondence with a picture produced with a simulator. Again, simple trigonometry shows that distance is given by the following equation:

$$Y = S_t(1 + d/S_t)/(1 - d/S_d). \tag{2}$$

Thus, this procedure eliminates the need for a simulator as a separate piece of equipment. Moreover, since both diagnostic and verification images are taken with the same equipment, the x-ray source 22, no correction of the verification images is required for comparison with the target area in the diagnostic image. The two sets of pictures are automatically available in the same scale, taken from the same point and perspective, and of the same acceptable quality. The only requirement is the parallax correction of the radiation field boundary produced by the treatment beam HR as a superimposed image on the detector, so that it is converted to the same scale of the verification image. Equation 1 above is used for this correction.

Finally, because this invention does not require movement of the patient or of the treatment unit, it is suitable for on-line, real-time, application, which renders it particularly valuable for radiation therapy. Many detectors exist that produce a real-time image, either directly or through computerized image enhancement processes. For example, FIG. 5 illustrates in schematic form the use of a fluorescent screen detector in conjunction with a mirror and a video camera to produce real-time verification images with the apparatus of the invention. By appropriately positioning the mirror (such as, for example, at a 45 degree angle with the detector), the video camera can be placed outside the therapeutic field of radiation (at a 90 degree angle with the detector), so that the image created on the fluorescent screen detector by the diagnostic beam is received by the video camera during the treatment session without interference. If the patient moves, the image on the detector will immediately reveal any change in the area being irradiated, so that immediate steps can be taken to minimize any localization error.

Note that radiation dosages during therapy are usually within the range of 3-10 cGy (rads), while a normal dose for diagnostic x-ray imaging purposes is usually within the range of 0.01-0.1 cGy (rads). Therefore, detector sensitivity at diagnostic energies is about two orders of magnitude higher than at therapeutic energies. Thus, the exposures form the therapeutic and diagnostic sources can easily be adjusted to obtain an optimal superimposed image of the radiation field (outlined by the shielding blocks) and of the patient's anatomy. In general, any thin detector currently available for radiation therapy imaging would be suitable to practice this invention. These include, without limitation, conventional films (with or without metal plates or fluorescent screens), photostimulable phosphors, scintillators of any type (glass, plastic, fiber optic, etc.), fluoroscopic screens, xeroradiographic devices, diode arrays, ionization chambers, and hydrogenated amorphous silicon sensors. Various other changes in the details, steps and materials that have been described may be made by those skilled in the art within the principles and scope of the invention herein illustrated and defined in the appended claims. Therefore, while the present invention has been shown and described herein in what is believed to be the most practical and preferred embodiments, it is recognized that departures can be made therefrom within the scope of the invention, which is therefore not to be limited to the details disclosed herein but is to be accorded the full scope of the claims so as to embrace any and all equivalent apparatus and methods.

What I claim is:

1. An imaging apparatus in combination with conventional radiation therapy equipment consisting of a gantry having a high-energy radiation source capable of emitting a high-energy radiation beam and having shielding blocks, said gantry being disposed for irradiation of a stationary patient positioned on a gurney at a fixed distance from the high-energy radiation source, said apparatus comprising the following components:

a low-energy radiation source capable of emitting a low-energy radiation beam and mounted on a side of the gantry opposite to the high-energy radiation source, such that the beam from said low-energy radiation source is coaxial with the beam from the high-energy radiation source; and a radiation detector mounted between the high-energy radiation source and the low-energy radiation source so as to be between the high-energy radiation source and the patient's gurney, said detector being positioned so that it can be exposed to both the high-energy beam and the low-energy beam;

wherein said low-energy radiation source and said detector are used to irradiate the patient and obtain diagnostic images of the patient before treatment with the high-energy beam and to obtain verification images of the patient's position for proper therapeutic irradiation during treatment.

2. The apparatus described in claim 1, wherein said low-energy radiation source consists of an x-ray tube.

3. The apparatus described in claim 1, wherein said radiation detector consists of a fluorescent screen.

4. The apparatus described in claim 1, further comprising a mirror positioned to receive the verification images formed on said radiation detector thereby forming corresponding images on said mirror and comprising a video camera positioned to receive the corresponding images formed on said mirror, so that the verification images created on the radiation detector are received by the video camera during a treatment session.

5. A method for producing corrected verification images of anatomical portions of a patient being treated with conventional radiation therapy equipment consisting of a gantry having a high-energy radiation source capable of emitting a high-energy radiation beam along a high-energy beam axis and having shielding blocks, said gantry being disposed for irradiation of a stationary patient positioned on a gurney at a fixed distance from the high-energy radiation source, a simulator of the radiation therapy equipment, and a shielding-block cutter, said method comprising the following steps:

(a) using the simulator of the radiation therapy equipment to produce diagnostic images of the patient from a field of view equal to the field of view of the high-energy radiation source;

(b) delineating the anatomical portions of the patient requiring treatment on said diagnostic images;

(c) using said shielding-block cutter to adapt the shielding blocks so that the high-energy source has a field of view limited to an area corresponding to the anatomical portions delineated on said diagnostic images;

(d) providing a low-energy radiation source mounted on a side of the gantry opposite to the high-energy radiation source, said low-energy radiation source being capable of emitting of low-energy radiation beam along a low-energy beam axis coaxial with the axis of the beam from the high-energy radiation source;

(e) providing a radiation detector mounted between the high-energy radiation source and the patient's gurney, said detector being positioned so that it can be exposed to both the high-energy beam and the low-energy beam;

(f) irradiating the patient with said coaxial low-energy radiation source during treatment to form verification images on said radiation detector;

(g) performing parallax corrections to the verification images so produced in order to obtain corrected verification images that are directly comparable to the diagnostic images produced during step (a); and (h) comparing the corrected verification images with the diagnostic images during treatment to ensure that the anatomical portions of the patient being irradiated by high-energy radiation treatment correspond to the anatomical portions delineated on the diagnostic images.

6. The method described in claim 5, wherein said parallax corrections are performed using the following relationship:

$$X_d = X_t(1 + d/S_t)/(1 - d/S_d),$$

where $S_t$ and $S_d$ are the distances of the high-energy radiation source and the low-energy radiation source, respectively, from the detector; $X_t$ is a distance between the axis of the high-energy beam and an image of an anatomical point back-projected by the high-energy beam on the radiation detector, and $X_d$ is a distance between the axis of the low-energy beam and the image of the same anatomical point projected by the low-energy beam on the radiation detector; and d is the distance between the anatomical point and the radiation detector.

7. The method described in claim 5, further comprising the steps of:

providing a mirror positioned to receive the verification images formed on said radiation detector thereby forming corresponding images on the mirror and providing a video camera positioned to receive the corresponding images formed on said mirror, so that the verification images created on the radiation detector are received by the video camera; and irradiating the patient during a treatment session to provide real-time verification of the patient's position to ensure that the anatomical portions being irradiated by high-energy radiation treatment correspond to the anatomical portions delineated on the diagnostic images.

8. A method for producing diagnostic and verification images of anatomical portions of a patient being treated with conventional radiation therapy equipment consisting of a gantry having a high-energy radiation source capable of emitting a high-energy radiation beam along a high-energy beam axis and having shielding blocks, said gantry being disposed for irradiation of a stationary patient positioned on a gurney at a fixed distance from the high-energy radiation source, and a shielding-block cutter, said method comprising the following steps:

(a) providing a low-energy radiation source mounted on a side of the gantry opposite to the high-energy radiation source, said low-energy radiation source being capable of emitting a low-energy radiation beam along a low-energy beam axis coaxial with the axis of the beam from the high-energy radiation source;

(b) providing a radiation detector mounted between the high-energy radiation source and the patient's gurney, said detector being positioned so that it can be exposed to both the high-energy beam and the low-energy beam;

(c) irradiating the patient with said coaxial low-energy radiation source to form diagnostic images of the patient on said radiation detector from a field of view corresponding to the low-energy radiation source;

(d) delineating the anatomical portions of the patient requiring treatment on said diagnostic images;

(e) using said shielding-block cutter to adapt the shielding blocks so that the high-energy source has a field of view limited to an area corresponding to the anatomical portions delineated on said diagnostic images;

(f) irradiating the patient with said coaxial low-energy radiation source during treatment to form corresponding verification images on said radiation detector; and (g) comparing the verification images with the diagnostic images during treatment to ensure that the anatomical portions of the patient being irradiated by high-energy radiation treatment correspond to the anatomical portions delineated on the diagnostic images.

9. The method described in claim 8, wherein said shielding block cutter comprises a high-energy radiation source simulator, a shielding blocks simulator and a radiation detector simulator, and wherein said step of adapting the shielding blocks so that the high-energy source has a field of view limited to an area corresponding to the anatomical portions delinated on the diagnostic images consists of positioning the high-energy radiation source simulator, the shielding blocks simulator and the radiation detector simulator exactly as the high-energy radiation source, the shielding blocks and the radiation detector are positioned in the radiation therapy equipment, and further consists of positioning the diagnostic images at a distance Y from the high-energy radiation source simulator in the shielding-block cutter given by the following equation:

$$Y = S_t(1 + d/S_t)/(1 - d/S_d),$$

where $S_t$ and $S_d$ are the distances of the high-energy radiation source and the low-energy radiation source, respectively, from the detector; and d is the distance between the anatomical portions and the radiation detector.

10. The method described in claim 8, further comprising the steps of:

providing a mirror positioned to receive the verification images formed on said radiation detector thereby forming corresponding images on the mirror and providing a video camera positioned to receive the corresponding images formed on said mirror, so that the verification images created on the radiation detector are received by the video camera; and irradiating the patient during a treatment session to provide real-time verification of the patient's position to ensure that the anatomical portions being irradiated by high-energy radiation treatment correspond to the anatomical portions delineated on the diagnostic images.

* * * * *